United States Patent [19]

Stein

[11] 4,406,286

[45] Sep. 27, 1983

[54] FAST RECHARGE OUTPUT CIRCUIT

[75] Inventor: Marc T. Stein, Tempe, Ariz.

[73] Assignee: Medtronic, Inc., Minneapolis, Minn.

[21] Appl. No.: 252,538

[22] Filed: Apr. 9, 1981

[51] Int. Cl.³ .............................................. A61N 1/36
[52] U.S. Cl. ........................................... 128/419 PG
[58] Field of Search .................... 128/419 PG, 419 PS

[56] References Cited

U.S. PATENT DOCUMENTS 3,707,974  1/1973  Naddi ............................ 128/419 PG
3,911,929 10/1975  Gobeli ........................... 128/419 PG

*Primary Examiner*—William E. Kamm

*Attorney, Agent, or Firm*—Joseph F. Breimayer; John L. Rooney; Robert C. Beck

[57] ABSTRACT

A body implantable stimulator having an output capacitance that is periodically charged to a predetermined energy level and discharged through an electrode coupled to body tissue. The discharge pulse width is controlled by a semiconductor switch and after a short delay the capacitor is recharged rapidly to its original charge. The recharge current is regulated by a differential circuit responsive to the voltage on a reference capacitor and the output capacitor, both capacitors being coupled to the active electrode.

18 Claims, 3 Drawing Figures

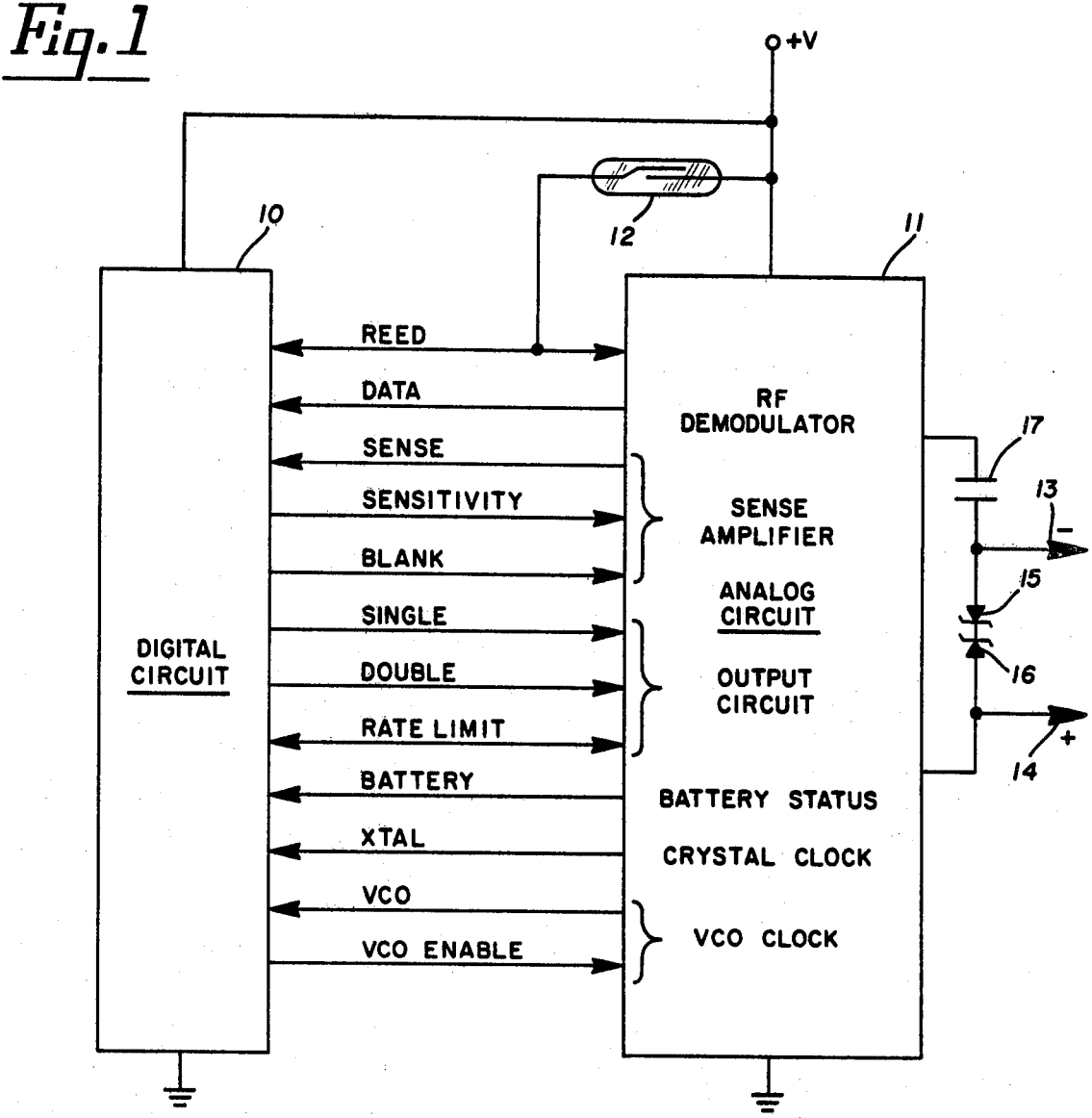
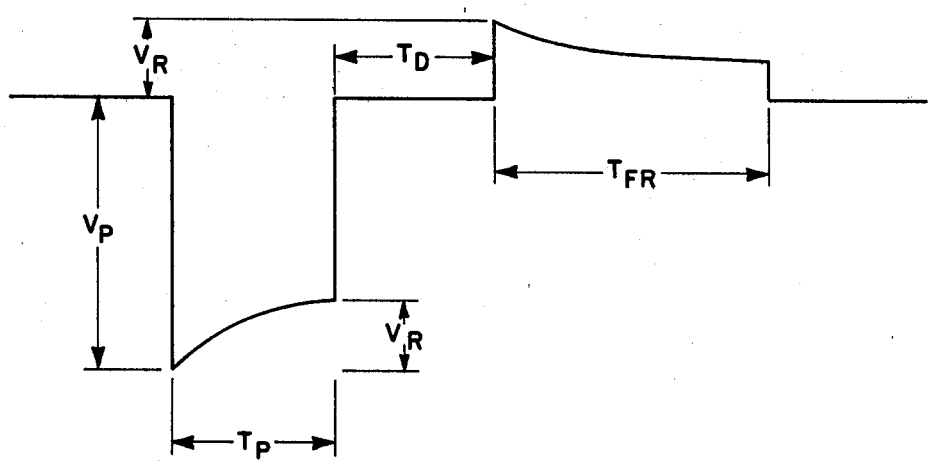

FAST RECHARGE OUTPUT CIRCUIT

BACKGROUND OF THE INVENTION

1. Field of the Invention

This invention relates to artifical cardiac pacemakers, either external or implantable having a sense amplifier for sensing natural heart signals.

2. Description of the Prior Art

The implantable cardiac pacemaker, shown in U.S. Pat. No. 3,057,356 and subsequent patents permits innocuous, painless, long-term cardiac stimulation at low power levels by utilizing a small completely implanted transistorized and battery operated pulse generator connected via a flexible lead bearing an electrode directly in contact with cardiac tissue. Most pulse generators consist of a stimulating circuit and a sensing circuit both of which draw current from the battery. In the presence of complete heart block, an asynchronous pulse generator with only a stimulating circuit may be used, however, in most instances, noncompetitive triggered or inhibited pulse generators having the sensing circuit are preferred and dominate the pacemaker market. The demand, synchronous or triggered pulse generators are especially useful in patients with spontaneous cardiac activity because of their ability to sense intrinsic cardiac rhythm (atrial or ventricular depending on variety and electrode position), and to alter the pacemaker output accordingly. Such pacemakers are shown for example, in U.S. Pat. Nos. 3,253,596 (P-wave synchronous), 3,478,746 (ventricular inhibited) and are described in the pacing literature.

More recently, attention has been paid to the physiological aspects of cardiac pacing therapy and particularly to pacing systems for maintaining synchronous atrial and ventricular depolarization of the heart. In early atrial synchronized (or A-V synchronous) pacing, atrial depolarization is sensed through one electrode, and after an appropriate delay the ventricle is paced through a different electrode, thereby restoring the normal sequence of atrial and ventricular contraction and allowing the pacer to respond to physiologic needs by increasing its rate. Below a predetermined minimal atrial rate, however, the pacemaker reverts to its basic ventricular pacing rate. In atrial synchronous, ventricular inhibited pacers of the type described in U.S. Pat. Nos. 4,059,116 and 3,648,707, the ventricular depolarizations are also sensed and inhibit or reset the timing of the ventricular stimulating pulse generator.

A more complex method of restoring synchrony is by the atrial ventricular sequential pacing of the type described in U.S. Pat. No. 3,595,242 and subsequent patents which possess atrial and ventricular pulse generators and associated electrodes and a ventricular sensing circuit. In atrial ventricular sequential pacing, the atria and ventricles are paced in proper sequence, the atrial and ventricular pulse generator timing circuits being reset on sensing spontaneous ventricular activity.

Finally, U.S. Pat. No. 4,312,355 and assigned to the assignee of the present invention, discloses a pacemaker which, if required, may stimulate the atrium and/or ventricle on demand and which is able to maintain synchrony as the sensed atrial rate increases. A pacemaker of this type is capable of distinguishing between bradycardia and normal heart function and to provide atrial and/or ventricular pacing in the following modes: inhibited in the case where the atrium and ventricle beat at a sufficient rate; atrial demand in instances where the atrium is beating at an insufficient rate and must be stimulated whereas the ventricle properly follows; atrial synchronous when the atrium depolarizes at a sufficient rate but the ventricle does not follow within a prescribed A-V interval; and dual demand when neither the atrium nor the ventricle spontaneously depolarize at the desired rate.

All of the demand pacemakers of the types described above comprise ventricular or atrial and ventricular timing circuits which may be a simple oscillator of the early designs or the complex, programmable design described in U.S. Ser. No. 235,069 filed Feb. 17, 1981, in the name of L. Herpers, which itself employs digital timing circuits of the type disclosed, for example, in the, analog sense amplifier circuits of the type disclosed, for example, in my co-pending U.S. Ser. No. 957,825 filed Nov. 6, 1978, and analog output circuits of the type disclosed, for example, in the copending U.S. Ser. No. 957,826 filed Nov. 6, 1978 in the name of David L. Thompson, all assigned to the assignee of the present invention. The inputs of the respective sense amplifiers and the output capacitances of the output circuits are commonly coupled to the respective atrial or ventricular sense amplifiers and through pacing leads to the electrodes coupled to the patient's heart.

The lead, the output circuit presented to the lead, the heart and the electrode-tissue interface comprise a capacitive-resistive reactance into which the stimulating pulse (the discharge of the output capacitor) is delivered. During the delivery of a stimulation signal, the output capacitor is partially discharged and recharges during the interval between stimulation signals. At higher rates, particularly with long duration signals, the capacitor may not fully charge during that interval. This potential problem could be accommodated by reducing the time constant of the charge path of the output capacitor. However, in the context of a demand cardiac pacemaker it is desirable to have a high impedance in that path in that a high input impedance, as viewed from the heart, aids in sensing R waves. However, this higher impedance increases the time constant and, thus, the time of recharge. The sense amplifier of a demand cardiac pacemaker senses this activity and, thus, it would be desirable to speed up the recharge of the output capacitor to shorten the recovery time of the sense amplifier.

The prolonged saturation period is especially troublesome in atrial and ventricular pacemakers where it is desirable to be able to sense atrial and ventricular heart activity after both atrial and ventricular stimulation. Attempts have been made in ventricular demand pacemakers to shorten the recharge period as shown, for example, in U.S. Pat. Nos. 3,835,865 and 4,170,999 and in the circuit disclosed in the aforementioned co-pending U.S. Ser. No. 957,826. None of these circuits are adequate for the purpose of decreasing the objectionable saturation-recharge period to a desirable interval, e.g. 10 ms, while retaining desired characteristics of the output circuit.

SUMMARY OF THE INVENTION

Accordingly, in recognition of the above stated disadvantages in the prior art the present invention provides an artificial body stimulator which possesses a fast recovery output circuit of a new design which recharges the output capacitor and reduces stimulation levels at the input of the sense amplifiers within a short interval.

Within the context of cooperating analog and digital circuitry for the generation and application of stimulating pulses, the present invention is directed to an output circuit for the provision of stimulation signals, the circuit being responsive to output initiate signals from the digital circuitry to establish the amplitude, duration and repetition rate of the stimulation signals while providing a fast recharge of the output capacitor following a stimulation signal and establishing an upper rate limit for the generation of output initiate signals by the digital circuitry and stimulation signals by the output circuit. In addition, the output circuit is responsive to a signal from the digital circuitry to establish an independent upper rate limit on the generation of stimulation signals. Of course, the output circuit could be coupled to an analog timing circuit and be triggered by a suitable oscillator. The circuit provides a high input impedance, as viewed from the body tissue being stimulated, while increasing the charge rate of the output capacitor for a predetermined period following each stimulation pulse under the control of the automatic fast recharge circuit of the present invention.

Briefly, the stimulating output circuit of the present invention comprises an output capacitance coupled to the output terminal, discharge circuit path means for providing a discharge current path through the output terminal, the lead conductor and electrode and the portion of the body stimulated and through a return path including a second electrode, and conductor and discharge switch means, recharge circuit path means comprising the same path with the exception of the discharge switch means and source of energy, and recharge control circuit means comprising a reference capacitance charged to the voltage of the output capacitance prior to its discharge and differential circuit means responsive to the difference between the reference and output capacitor voltages for closing the recharge switch means until the voltage levels are equalized. Preferably delay circuit means is provided for establishing a short delay between the discharge and recharge of the output capacitor. Furthermore the recharge voltage source providing the recharge current may be a multiple of the source voltage to further shorten the recharge period. The output pulse thus assumes the appearance of a biphasic pulse with a short step delay between the opposite polarity deviation of the pulse.

Stated in another manner the invention involves a method and apparatus for recharging the output capacitor to a reference level independent of the load presented, the width and amplitude of the discharge pulse, and the interval between pulses through the steps of discharging the output capacitor, comparing the residual voltage level on the output capacitor to a reference voltage level, recharging the output capacitor to a voltage equal to the reference voltage and terminating the recharging current.

In the preferred embodiment of the invention employing a programmable digital oscillative circuit, the digital circuitry generates an output initiate signal in the form of a SINGLE or DOUBLE signal. Each output initiate signal results in the provision of a stimulation signal by the output circuit, the repetition rate and duration of the stimulation signal being established by the repetition rate and duration of the output initiate signal, respectively. The amplitude of the stimulation signal is dependent on the output initiate signal generated by the digital circuitry. For example, the generation of a DOUBLE signal results in a stimulation signal having an amplitude approximately twice the supply voltage. A SINGLE initiate signal results in a stimulation signal having an amplitude approximately equal to the supply voltage. Thus, the output circuit of the present invention will provide stimulation signals having an amplitude established by the output initiate signals generated by the digital circuitry. The ability to alter the stimulation signal amplitude, duration and repetition rate provides great flexibility in establishing the operating parameters during normal operation as well as during testing of the stimulator and its interaction with the body.

The foregoing and additional advantages and characterizing features of the present invention will become clearly apparent upon reading of the ensuing detailed description of an illustrative embodiment thereof together with the included drawings depicting this theme.

BRIEF DESCRIPTION OF THE DRAWINGS

FIG. 1 shows the interconnection and cooperation between the digital circuit of the incorporated specification and a cooperating analog circuit of which the present invention is a part;

FIG. 3 illustrates the output pulse and recharge waveform at the terminals 13-14 of FIG. 2.

DETAILED DESCRIPTION OF THE INVENTION

Figure 2:
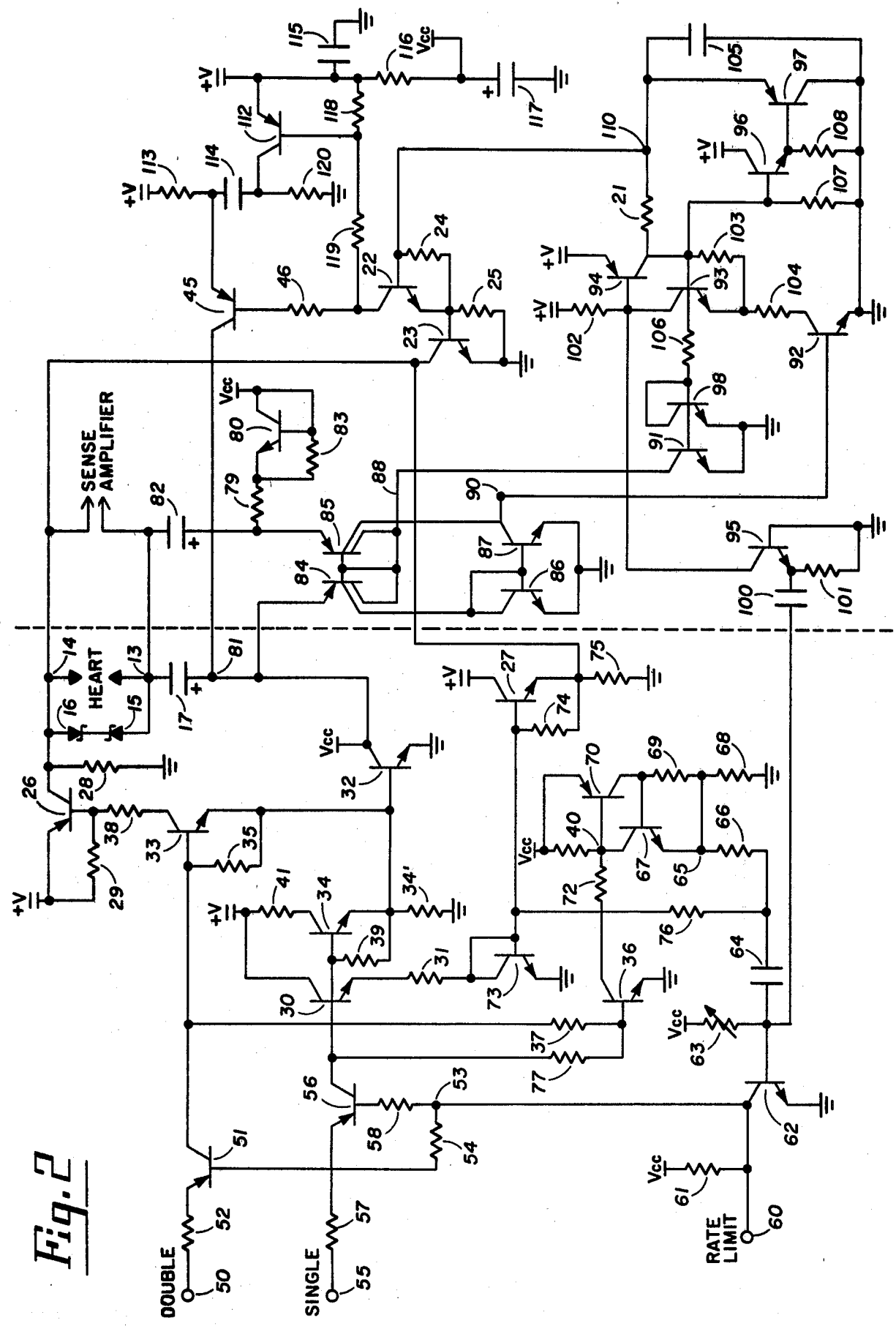
FIG. 2 shows the circuitry of an output circuit forming a part of the analog circuitry of FIG. 1.

Referring now to FIG. 1 there is shown a block diagram illustrating the interconnections between Digital Circuitry 10 (as disclosed in the incorporated specification) and Analog Circuitry 11 (of which the present invention is a part). Both the Digital Circuit 10 and Analog Circuit 11 are connected between a source of positive potential V+ and a reference potential, such as ground. The source of positive potential may be a battery such as the conventional lithium iodide battery which generates approximately 2.8 volts.

The Analog Circuit 11 consists of various distinct electrical systems which may be referred to functionally as an RF Demodulator, a Sense Amplifier, an Output Circuit, a Battery Monitor and Status Indicator, a Crystal Clock and a Voltage Controlled Oscillator Clock. The Digital Circuit 10 includes all of the digital logic necessary to cause a programming change, memory to store the digital code manifesting the desired values for the program parameters and digital timing means for causing a stimulation pulse to be generated in the programmed manner. The signals applied between the Digital Circuit 10 and Analog Circuit 11 are REED, DATA, SENSE, SENSITIVITY, BLANK, SINGLE, DOUBLE, RATE LIMIT, BATTERY, XTAL, VCO and VCO ENABLE.

A magnetically actuated reed relay switch 12 is connected between the source of positive potential V+ and both the Digital Circuit 10 and the RF Demodulator of Analog Circuit 11. Reed switch 12 is normally open and is closed as by placing a magnet in close proximity thereto. When closed, a V+, or logic "1", REED signal is applied to both the Digital Circuit 10 and Analog Circuit 11. On removal of the magnet, the reed switch 12 opens and a ground, or logic "0" signal is applied to the Digital Circuit 10 and Analog Circuit 11. The RF Demodulator is enabled by a V+ REED signal produced by a closing of the reed switch 12 to provide a DATA signal to the digital circuit 10. The DATA signal (the Digital Circuit 10 programming signal) is a pulse signal going from logic "0" to logic "1", as described in the incorporated specification, which is representative of pulse bursts generated externally.

The Sense Amplifier portion of the Analog Circuit 11 provides a SENSE signal each time natural heart activity is detected to restart the timing cycle of the Digital Circuit 10, when operating in a demand mode. A SENSITIVITY signal is provided by the Digital Circuit 10 in accordance with its programming to establish the detection level of the Sense Amplifier. A BLANK signal is generated by the Digital Circuit 10 and applied to the Sense Amplifier portion of the Analog Circuit 11 to establish the refractory period of the Sense Amplifier and to allow the components within the Sense Amplifier to reset themselves.

The Output Circuit of Analog Circuit 11 includes output terminals 13 and 14 which are adapted for connection to a conventional lead, in a known manner. The output terminal 14 may be connected to a metal case housing the pacemaker unit or a plate forming a part of the case in a unipolar lead system or it may be connected to a second lead in a bipolar lead system, depending on the type of lead system employed. Output terminal 13 is coupled through a capacitor 14 to the Analog Output Circuit and to the heart (not shown). In addition, a pair of Zener diodes 15 and 16 have their anodes coupled together and their cathodes coupled to output terminals 13 and 14, respectively. Diodes 15 and 16 function in a conventional manner to prevent damage to the pacemaker circuitry in the presence of large extraneous signals such as are caused by electrocautery. The Output Circuit of Analog Circuit 11 includes elements responsive to a SINGLE or DOUBLE signal from Digital Circuit 10 to control the amplitude of output signals applied across output terminals 13 and 14. The Output Circuit of Analog Circuit 11 provides a RATE LIMIT signal to Digital Circuit 10 to provide an upper limit to the rate at which stimulation initiating signals are generated. Digital Circuit 10 also provides a rate limit disable signal to the Output Circuit of Analog Circuit 11 to eliminate the upper limit to the rate at which stimulation pulses may be applied by the Output Circuit.

In addition to the above, Analog Circuit 11 includes circuitry which monitors the status of the battery to provide an indication of that status in the form of the BATTERY signal. Also, clock pulses are provided to the Digital Circuit 10 in the form of signals XTAL and VCO. Within the context of the Digital Circuit of the incorporated specification, the XTAL signal is a generally square wave pulse signal occuring at a frequency of 32,768 Hz and the VCO signal is a square wave pulse signal having a preset frequency when V+ is equal to 2.8 volts. As V+ decreases over time, with battery depletion, the frequency of the VCO signal will also decrease, in known manner. The VCO signal is used in the timing circuitry of Digital Circuit 10 to establish the exact width of stimulating pulse. In order to maintain a constant energy of this pulse, it is necessary that the pulse increase in width as V+ decreases. The VCO clock pulse generator is enabled only during the time the stimulating pulse is to be provided and is enabled by the signal VCO ENABLE.

Unlike the circuit shown in the aforementioned U.S. Ser. No. 940,694, the present invention does not rely on a RECHARGE signal from the Digital Circuit 10. In this invention, recharge is accomplished by the circuitry in the Analog Circuit 11 to be described in reference to FIGS. 2 and 3.

Referring now to FIG. 2 there is shown a preferred embodiment of the output circuit of the present invention with the numerals 13-17 referencing the same elements as illustrated in FIG. 1. Similarly, elements through numeral 72 correspond to elements used in the circuit of the aforementioned U.S. Ser. No. 957,826 and the remaining elements from numeral 73 differ from that circuit. The principal differences between the two circuits reside in the automatic fast recharge circuit of the present invention, generally on the left side of the dashed line drawn from top to bottom in FIG. 2.

In general the circuitry on the left side of the dashed lines in FIG. 2 operates as follows. In this drawing, V+ is a source of positive potential. Vcc indicates a positive potential source that is filtered to prevent the ripple caused by a stimulation pulse from turning on the rate limit circuitry in the middle of a stimulation pulse and thus cause a loss of a part of the stimulation pulse. A terminal 50 is adapted for connection to receive a DOUBLE signal from Digital Circuit 10 and is connected to the emitter of a transistor 51 via a resistor 52. The collector of transistor 51 is connected to the base of transistor 33 while its base is connected to a junction 53 via resistor 54. A terminal 55 is adapted for connection to receive the SINGLE signal from the Digital Circuit 10 and is connected to the emitter of a transistor 56 via resistor 57. The collector of transistor 56 is connected to the base of transistor 34 while its base is connected to junction 53 via resistor 57. A terminal 60 is adapted for connection to receive the RATE LIMIT signal from Digital Circuit 10 and is connected to a positive potential Vcc via resistor 61 and to the collector of a transistor 62 and and the junction 53. The emitter of transistor 62 is connected to ground and its base is connected to Vcc via a resistor 63 and to a capacitor 64. The capacitor 64 is connected to a junction 65 via a resistor 66, the junction 65 being connected to the emitter of a transistor 67 and to ground via a resistor 68 and to the base of transistor 67 via a resistor 69. The base of transistor 67 is connected to the collector of a transistor 70 while its collector is connected to the junction 40. The emitter of transistor 70 is connected to Vcc and to its base and junction 40 via a resistor 71. The collector of transistor 36 is connected to junction 40 via resistor 72.

A DOUBLE signal appearing at terminal 50 will result in a stimulation signal at terminals 13 and 14 at approximately twice the potential of V+. The DOUBLE signal is a positive pulse having a duration that is essentially the duration of the desired stimulation pulse. This pulse turns on transistor 51 resulting in the turn on of transistor 33. The turn on of transistor causes transistors 26 and 32 to saturate. Assuming that capacitor 70 had charged to V+, the conduction of transistor 32 connects the positive terminal of capacitor 17 to ground driving its negative terminal 13 negative. The conduction of transistor 26 connects terminal 14 to V+ and, accordingly, the voltage across terminal 13 and 14 is V+ −(−V+)=2V+. In practice, of course, saturation losses will result in a slightly lower voltage applied across the terminals 13 and 14.

The SINGLE signal applied to terminal 55 is a positive pulse having a duration essentially that of the desired stimulation pulse. This signal turns on transistor 56 which turns on transistors 30, 32 and 34. The conduction of transistor 34 again causes transistor 32 to saturate and force the terminal 13 negative. The conduction of transistor 30 also turns on transistor 37. However, the emitter of transistor 27 is clamped at ground potential due to the fact that the base emitter voltage of transistor 34 plus that of transistor 32 must equal the base emitter voltage of transistor 30 plus that of transistor 27. Thus, terminal 14 is maintained at ground potential and approximately the negative of V+ is applied across the terminals 13 and 14. Again, of course, the saturation losses in transistor 32 reduces the potential across the terminals 13 and 14 by a small amount.

During the stimulation pulse resulting from the SINGLE output initiate signal, transistor 32 is saturated while transistor 27 is in its linear range. Thus, at the end of the SINGLE signal, transistor 27 would be expected to turn off faster than transistor 32. In that case, terminal 13 would still be negative when transistor 27 turns off resulting in a path for current flow through the body tissue connected between terminals 13 and 14 and resistor 28 producing a negative spike on the collector of transistor 23. Resistor 31 eliminates this spike by providing a low impedance path for the base of transistor 32 which allows transistor 32 and 27 to turn off simultaneously.

Transistor 62 is normally saturated resulting in a "zero" or ground condition at terminal 60. A positive signal applied to the terminal 60 disables the transistors 51 and 56 and prevents them from turning on in response to an output inititate signal. In essence, such a condition blocks the output inititate signals. Within the output circuit of the present invention, a positive signal on terminal 60 is obtained, via resistor 61, when transistor 62 is "off". Conduction of transistor 62 causes its collector to go to ground potential thus enabling transistors 51 and 56 and, accordingly, the output circuit of FIG. 2. The signal at terminal 62 resulting from the turn on and turn off of transistor 62 may also be applied as the RATE LIMIT signal to the digital circuit 10 to enable and disable the generation of output initiate signals. Accordingly, the turn off of transistor 62 may be employed as a disable signal in the digital circuit 10 to prevent the generation of output initiate signals thereby providing an additional upper rate limit.

The appearance of a SINGLE or DOUBLE output initiate signal results in a signal at junction 40 and the conduction of transistors 67 and 70. For example, a DOUBLE signal at terminal 50 will turn on transistor 51 resulting in the conduction of transistor 36 and a signal at junction 40. Likewise, a SINGLE signal at terminal 55 will render transistor 56 and then transistor 36 conductive and produce a signal at junction 40. In either event, a signal at junction 40 results in the turn on of transistors 67 and 70 which are connected in a SCR arrangement. Once conductive, the circuit of transistors 67 and 70 will remain on until capacitor 64 is charged and the SINGLE or DOUBLE output initiate signal terminates. Thus, the on time of transistors 67 and 70 is established by the duration of the output initiate signal with the charge time of capacitor 64 setting a minimum "on" time. On termination of the SINGLE or DOUBLE output initiate signal, with capacitor 64 charged, the transistors 67 and 70 will turn off returning the right side of capacitor 64 to ground via resistors 66 and 68. Since the voltage across capacitor 64 cannot change instantaneously, the base of transistor 62 is driven negative cutting it off and causing its collector to go positive. This positive signal at the collector of transistor 62 disables the transistors 51 and 56 and may be employed as a RATE LIMIT disable signal within the analog circuit 10. With transistors 67 and 70 off, capacitor 64 charges toward Vcc through resistors 63, 66 and 68 until the base of transistor 62 is forward biased. At that time, transistor 62 turns on putting a zero condition at terminal 60, again enabling transistors 51 and 56. The maximum output stimulation rate is thus limited by the time that transistor 62 is off, that time being established by the time constant of the circuitry including capacitor 64 and resistors 63, 66 and 68 and being selectable at any desired rate, in known manner. It should be noted that the transistors 67 and 70 stay on for at least the duration of a SINGLE or DOUBLE output initiate signal which prevents the turn off of transistor 62 during those signals and, thus, prevents the disruption of a stimulation signal.

The circuit of FIG. 2 is intended for use in the atrial and ventricular pulse generator and the circuitry to the left of the dashed lines will accordingly be duplicated and appear in both the atrial and ventricular output channels. The pulse generator case acts as the indifferent electrode for both the atrial and ventricular stimulating electrodes. This common connection could cause the atrial and ventricular output pulses to cause spurious signals within the ventricular and atrial output circuits respectively. To avoid this potential problem, the circuit of FIG. 2 (left of the dashed line) includes additional components to the corresponding circuit in the aforementioned U.S. Ser. No. 957,826. Thus, the transistor 73 (connected as a diode) provides a diode drop to ground through the resistor 74 and base-emitter of transistor 27, so that a spurious reflected voltage from output terminal 14 (through conductor 121) will not be capable of rendering transistor 27 conductive and thus triggering an output pulse. In addition, the resistor 76 provides a bias voltage to the base of transistor 27 during the time delay ($T_D$ in FIG. 3) between the pacing and recharging pulses. This keeps the indifferent electrode 14 (case of the pulse generator) from going below ground potential due to polarization voltages by biasing transitor 27 conductive during that interval. During the delivery of a stimulation signal, capacitor 17 is partially discharged—typically on the order of 0.5 volt. A short time after the stimulation signal has ended the automatic recharge circuitry to the right of the dashed line in FIG. 2 commences to recharge the output capacitor 17 in a manner to be described. In general, transistor 22 is rendered conductive and causes transistors 45 and 23 to saturate allowing capacitor 17 to charge quickly through transistor 23, the body tissue connected between terminals 13 and 14 and transistor 45. During the fast recharge interval, capacitor 17 charges to approximately V+ less saturation losses in transistors 45 and 80. Those transistors may be selected to minimize the saturation losses and thus maximize the charge on capacitor 17. Resistor 28 allows the continued charging of capacitor 17 after the fast recharge interval until the next output pulse is initiated. Thus, the output circuit of the present invention provides means for increasing the charge rate of the output capacitor by providing first and second charge paths for the capacitor, one charge path being selectively conductive and of a lower impedance than the other path. In the illustrated embodiment, transistor 23 provides a low impedance path across resistor 28 within the normal capacitor charge path thereby reducing the impedance and time constant of the charge path during the time that the recharge current is applied to the terminal 21. A high impedance is maintained at all other times as an aid in sensing R waves.

More specifically, the automatic fast recharge circuitry comprises a parallel reference capacitor 82 of lower capacitance than the output capacitor 17 coupled to terminal 13 and to a charging current source comprising the regulated source $V_{cc}$, transistor 80 and resistors 79 and 83. The reference capacitor 82 is charged through the reactance of the heart and the lead and electrode and the charge/discharge path of the output capacitor 17 to a reference voltage roughly comparable to the regulated voltage $V_{cc}$. The capacitors 17 and 81 are coupled to a differential circuit comprising transistors 84 to 87 which, when rendered conductive by a signal on conductor 88, develop a recharge control current signal at terminal 90. The transistors 84–87 are rendered capable of conducting when the collectors and base terminals of transistors 84 and 85 are pulled to ground potential through conduction of transistor 91 in a manner to be described. When transistors 84 and 85 are rendered conductive, the active load comprising the transistors 86 and 87 likewise tend to conduct. As long as the voltages on capacitors 17 and 82 differ, an output current proportional to that difference is developed at terminal 90.

For physiological reasons and to assist in the analysis of the waveform of the pulse generator, it is desirable to introduce a short delay interval between the termination of the output pulse and the commencement of the fast recharge current. This is accomplished by the trigger and delay circuit comprising the transistors 91–98 and the associated components. A capacitor 100 is coupled to one terminal of capacitor 64 which, as described herinbefore, is discharged during the provision of the output pulse and after its subsequent recharge renders transistor 62 nonconductive. The capacitor 100 is charged through the resistors 63 and 101 to the regulated voltage level. Capacitor 100 is similarly discharged on conduction of transistor 62 thereby drawing a negative current at the emitter of transistor 95 and turning it on momentarily. The conduction of transistor 95 renders the SCR switch, comprising transistors 93 and 94 and resistors 102 and 103 conductive and thereby applies source voltage to transistor 92 through resistor 104. If the difference current then exists at the terminal 90, the transistor 92 is rendered conductive thereby maintaining the conduction of the SCR switch as long as transistor 92 remains conductive.

The conduction of transistor 94 provides a source voltage through resistor 106 to the base of transistor 98 (functioning as a diode) and transistor 91 to render transistor 91 conductive and thereby draw down the collectors of transistors 84 and 85 rendering the latter transistors capable of conducting. The conduction of transistors 84 and 85 thus allows the difference current to be generated at the terminal 90 to thereby maintain transistor 92 conductive.

The conduction of transistor 94 also allows source current to flow through the resistor 21 and into the load capacitor 105 to provide a time delay before the recharge of the output capacitor 17 can commence. The conduction of transistor 94 also renders transistor 96 conductive which applies source voltage to the base of transistor 97 and renders transistor 97 nonconductive. When transistors 94 and 96 are no longer conductive, the charge on capacitor 105 is discharged through the then conductive transistor 97.

The values of resistor 21 and capacitor 105 are selected to provide a desired time delay before the voltage at terminal 110 is sufficient to render the transistors 22, 23 and 45 conductive. The voltage at terminal 110 is reflected upon the base of transistor 22 and through resistor 214 to the base of transistor 23. When transistor 24 is rendered conductive it draws down the voltage at the base of transistor 45 and transistor 112 thus rendering them conductive. The elements 112–120 constitute a voltage multiplier which upon conduction of transistor 112, presents a voltage equal to twice the supply of voltage at the terminal 81 to rapidly recharge the output capacitor 17. Prior to the conduction of transistors 45 and 112, the capacitors 114, 115 and 117 are charged to supply voltage in parallel charging circuits. On conduction of transistor 112, the voltages on the capacitors 114 and 115 are summed to present the high recharging voltage.

The conduction of transistor 45 provides a rapid recharging current to capacitor 17 through the terminal 81, the output terminal 13, the lead, electrode and patient's heart (not shown) and return or indifferent electrode and lead (if any) coupled to terminal 14, and the collector-emitter path of transistor 23 which is simultaneously rendered conductive by the conduction of transistor 22. The conduction of transistor 23 thus bypasses the resistance 28 and allows for a low resistance recharge path.

The conduction of transistor 23 simultaneously presents a ground potential on conductor 121 which is coupled to the emitter of transistor 27 thus rendering transistor 27 incapable of conducting.

The recharging current applied at terminal 81 rapidly recharges the capacitor 17 until its voltage begins to equal the voltage on the reference capacitor 82 whereupon the differential circuit can no longer sustain the difference current at terminal 90. When that happens, transistor 92 is no longer conductive, and the transistors 93, 94, 96, 98 and 91 are thereby turned off. Thereupon, the charge on capacitor 105 begins to discharge through transistor 37, and the remaining transistors 84–87 and 22, 23, 45 and 112 are all turned off. Thus, all active elements in the fast recharge circuit cease drawing the source current as soon as the recharge is accomplished.

The output pulse and the recharge pulse as measured at the terminals 13–14 are shown in the waveform drawing of FIG. 3. The output pulse is a negative pulse which decays exponentially as a function of the discharge of capacitor 17. The amount that capacitor 17 discharges is a function of the pulse width $T_p$ and the electrode-heart tissue reactance and in the illustration is an amount designated as $V_R$. The delay interval $T_D$ is the interval set by resistor 21 and capacitor 105 which is ordinarily about 0.5 ms. The fast recharge period $T_{FR}$ is set ordinarily at 6–12 ms.

The fast recharge waveform 1 as shown in the drawing would appear at the terminals 13–14 as an opposite polarity voltage pulse with an initial amplitude $V_R$ equal to the discharge of the capacitor 17. Of course, a higher voltage in the order of 2V+ is applied at the terminal 81 during the fast recharge period $T_{FR}$ to provide a high recharge current source. The voltage of the fast recharge waveform depicted decreases as the capacitor 17 is recharged to a level that does not interfere with the detection of heart signals.

In summary, a fast recharge circuit for body tissue stimulator that rapidly restores a stable base signal level on the output terminals and the sense amplifier input terminals has been described. Detection of heart (or body tissue) signals is made easier after the fast recharge period as the level of recharge current is lower than heart signal levels encountered in practice. In addition, the balanced, reverse polarity signals may to some extent decrease electrode deterioration due to ion migration of the metallic surface.

Although the new output circuit has been described in the context of a digital control pacemaker timing circuit, it will be recognized that it can as well be utilized in heart pacemakers of any of the known types, analog or digital, that employ sense amplifiers whether synchronous, demand, atrial or ventricular or combinations thereof. Preferably the fast recharge circuit is employed in the atrial sense amplifier of a dual pace, dual sense pacemaker of the type described in the aforementioned U.S. Pat. No. 4,312,355 which is implemented employing the components of the aforementioned incorporated applications. In addition, fast recharge circuit may be advantageously employed in body tissue stimulators of other types, e.g. nerve or deep brain stimulators. It is therefore to be understood that, within the scope of the appended claims, the invention may be practiced otherwise than as specifically described.

I claim:

1. A body implantable stimulator of the type having power source means, pulse generator means for producing body stimulation signals and output means adapted for connection to the body for the delivery of said stimulation signals thereto comprising:

means for storing stimulation energy connected to said output means;

discharge circuit means for periodically discharging said stimulation energy storing means into said output means for providing said stimulation signals; and recharge circuit means for recharging said stimulation energy storing means from said power source means to a predetermined level further comprising:

(1) means for storing reference energy connected to said output means;

(2) differential circuit means coupled to said stimulation energy storing means and said reference energy storing means for developing a difference signal dependent upon the difference in energy therebetween; and (3) recharge current source means responsive to said difference signal for providing a recharge current to said stimulation energy storing means until the energy levels of said stimulation energy storing means and said reference level energy storing means are substantially equivalent, whereby said stimulation energy storing means is recharged to said reference level regardless of the energy discharged by said discharge circuit means.

2. The stimulator of claim 1 wherein said recharge circuit means further comprises time delay circuit means for delaying the recharging of said stimulation energy storing means for a predetermined interval.

3. The stimulator of claim 2 wherein said stimulation and reference energy storing means each comprise a capacitor adapted to be charged to a predetermined voltage and commonly coupled to an output terminal of said output means.

4. The stimulator of claim 2 wherein said recharge current source means further comprises voltage multiplication means for providing said recharge current from a recharge voltage source which is a multiple of the voltage of said power source means.

5. The stimulator of claim 2 wherein said discharge circuit means further comprises a load impedance coupled to said stimulation energy storing capacitor means for presenting a high impedance to said output means; and said recharge circuit means further comprises means responsive to said difference signal for shunting said lead impedance to reduce the effective impedance of said load impedance in circuit with said stimulation energy storing capacitor means during recharge thereof.

6. The stimulator of claim 1 wherein said stimulation and reference energy storing means each comprise a capacitor adapted to be charged to a predetermined voltage and commonly coupled to an output terminal of said output means.

7. The stimulator of claim 3 wherein said recharge current source means further comprises voltage multiplication means for providing said recharge current from a recharge voltage source which is a multiple of the voltage of said power source means.

8. The stimulator of claim 1 wherein said recharge current source means further comprises voltage multiplication means for providing said recharge current from a recharge voltage source which is a multiple of the voltage of said power source means.

9. Apparatus for recharging the stimulation energy storing capacitor of a body tissue stimulator of the type having power source means, pulse generator means for producing body stimulation signals and output means adapted for connection to the body for the delivery of said stimulation signals thereto, said apparatus further comprising:

means for periodically discharging the capacitor voltage into body tissue for a first predetermined time interval;

means for establishing a reference voltage level related to the capacitor voltage prior to its discharge;

means for comparing the residual voltage level on the capacitor at the end of the time interval to said reference voltage level; and means for recharging the capacitor to a voltage equal to said reference voltage level during a second predetermined time interval.

10. The apparatus of claim 9 wherein said comparing means comprises differential circuit means coupled to said stimulation energy storing capacitor and said reference voltage level for developing a difference signal dependent upon the difference in energy therebetween; and said recharging means is responsive to said difference signal for providing a recharge current to said stimulation energy storing capacitor until the energy levels of said stimulation energy storing capacitor and said reference level energy storing means are substantially equivalent, whereby said stimulation energy storing capacitor is recharged to said reference level regardless of the energy discharged by said stimulation energy storing capacitor into body tissue.

11. The apparatus of claim 10 wherein said recharging means further comprises time delay circuit means for delaying the recharging of said stimulation energy storing means for a predetermined interval.

12. The apparatus of claim 11 wherein said recharging means further comprises voltage multiplication means for providing a recharge current from a recharge voltage source which is a multiple of the voltage of said power source.

13. The apparatus of claim 10 wherein said reference voltage level means also comprises a capacitor adapted to be charged to a predetermined voltage and commonly coupled to an output terminal of said output means with said energy storing capacitor.

14. The apparatus of claim 10 wherein said recharging means further comprises voltage multiplication means for providing a recharge current from a recharge voltage source which is a multiple of the voltage of said power source.

15. The apparatus of claim 10 wherein said discharging further comprises a load impedance coupled to said stimulation energy storing capacitor; and further comprising means responsive to said recharging means for shunting said load impedance to reduce the effective impedance of said load impedance in circuit with said stimulation energy storing capacitor during recharge thereof.

16. The apparatus of claim 9 wherein said reference voltage level means also comprises a capacitor adapted to be charged to a predetermined voltage and commonly coupled to an output terminal of said output means with said energy storing capacitor.

17. The apparatus of claim 9 wherein said recharging means further comprises voltage multiplication means for providing a recharge current from a recharge voltage source which is a multiple of the voltage of said power source.

18. The apparatus of claim 9 wherein said discharging further comprises a load impedance coupled to said stimulation energy storing capacitor; and further comprising means responsive to said recharging means for shunting said load impedance to reduce the effective impedance of said load impedance in circuit with said stimulation energy storing capacitor during recharge thereof.

* * * * *

UNITED STATES PATENT AND TRADEMARK OFFICE
CERTIFICATE OF CORRECTION

PATENT NO. : 4,406,286
DATED : September 27, 1983
INVENTOR(S) : Marc T. Stein

It is certified that error appears in the above-identified patent and that said Letters Patent are hereby corrected as shown below:

Column 2,
    Line 14, delete second "the" and insert --U.S. Pat. No. 4,250,883--;

Column 6,
    Line 2, "940,694" should be --957,826--;

Line 58, "70" should be --17--;

Column 7,
    Line 5, "37" should be --27--;

Line 39, "62" should be --60--.

Signed and Sealed this

Twenty-seventh Day of December 1983

[SEAL]

Attest:

GERALD J. MOSSINGHOFF

Attesting Officer    Commissioner of Patents and Trademarks